US008376988B2

(12) United States Patent
Perovitch

(10) Patent No.: US 8,376,988 B2
(45) Date of Patent: Feb. 19, 2013

(54) DEVICE FOR PACKAGING AND SUBLINGUAL ADMINISTRATION OF ACTIVE PRINCIPLES

(76) Inventor: Philippe Perovitch, Le Temple (FR)

( * ) Notice: Subject to any disclaimer, the term of this patent is extended or adjusted under 35 U.S.C. 154(b) by 167 days.

(21) Appl. No.: 12/668,805

(22) PCT Filed: Jul. 18, 2008

(86) PCT No.: PCT/FR2008/051368

§ 371 (c)(1),
(2), (4) Date: Jan. 12, 2010

(87) PCT Pub. No.: WO2009/016309

PCT Pub. Date: Feb. 5, 2009

(65) Prior Publication Data

US 2010/0198147 A1 Aug. 5, 2010

(30) Foreign Application Priority Data

Jul. 20, 2007 (FR) ..................................... 07 05290

(51) Int. Cl.
*A61M 37/00* (2006.01)
*B65D 25/08* (2006.01)
*B67D 1/00* (2006.01)

(52) U.S. Cl. ............................. 604/88; 206/222; 222/83

(58) Field of Classification Search ............. 222/153.01, 222/153.03, 83; 604/48, 77, 82, 87, 88, 91, 604/92, 310
See application file for complete search history.

(56) References Cited

U.S. PATENT DOCUMENTS

| | | | | |
|---|---|---|---|---|
| 2,754,590 | A | 7/1956 | Cohen | |
| 3,802,604 | A * | 4/1974 | Morane et al. | 222/83 |
| 4,648,532 | A * | 3/1987 | Green | 222/82 |
| 4,722,449 | A * | 2/1988 | Dubach | 215/235 |
| 4,898,293 | A * | 2/1990 | Morel | 215/250 |
| 4,982,875 | A * | 1/1991 | Pozzi et al. | 222/83 |
| 5,932,235 | A | 8/1999 | Ninomiya et al. | |
| 2003/0045579 | A1 * | 3/2003 | Leone-Bay et al. | 514/562 |
| 2004/0074925 | A1 | 4/2004 | Faurie | |

FOREIGN PATENT DOCUMENTS

| | | | |
|---|---|---|---|
| DE | 42 19 103 | A1 | 12/1993 |
| EP | 0 293 290 | A | 11/1988 |
| EP | 1 086 661 | A2 | 3/2001 |
| FR | 800 987 | A | 7/1936 |
| WO | 91/13814 | A | 9/1991 |
| WO | 95/25948 | A | 9/1995 |
| WO | 97/25024 | A1 | 7/1997 |
| WO | 02/38464 | A1 | 5/2002 |

* cited by examiner

*Primary Examiner* — Nicholas Lucchesi
*Assistant Examiner* — Leah Stohr
(74) *Attorney, Agent, or Firm* — Sughrue Mion, PLLC

(57) ABSTRACT

The invention provides a container for preparing and/or administering a very small volume of active principles in liquid form, the container comprising a head (12) suitable for taking up a conservation, first position P1 in which said head (12) is in a distal position relative to the container, and an administration, second position P2 in which said head (12) is in a proximal position relative to the container, said head (12) including a cannula (14) with at least one flow channel (16), its length being adapted so that the free end of the flow channel (16) can enable delivery by sublingual and/or paragingival permeation, while the container is being held in the hand.

21 Claims, 3 Drawing Sheets

DEVICE FOR PACKAGING AND SUBLINGUAL ADMINISTRATION OF ACTIVE PRINCIPLES

Figure 1:
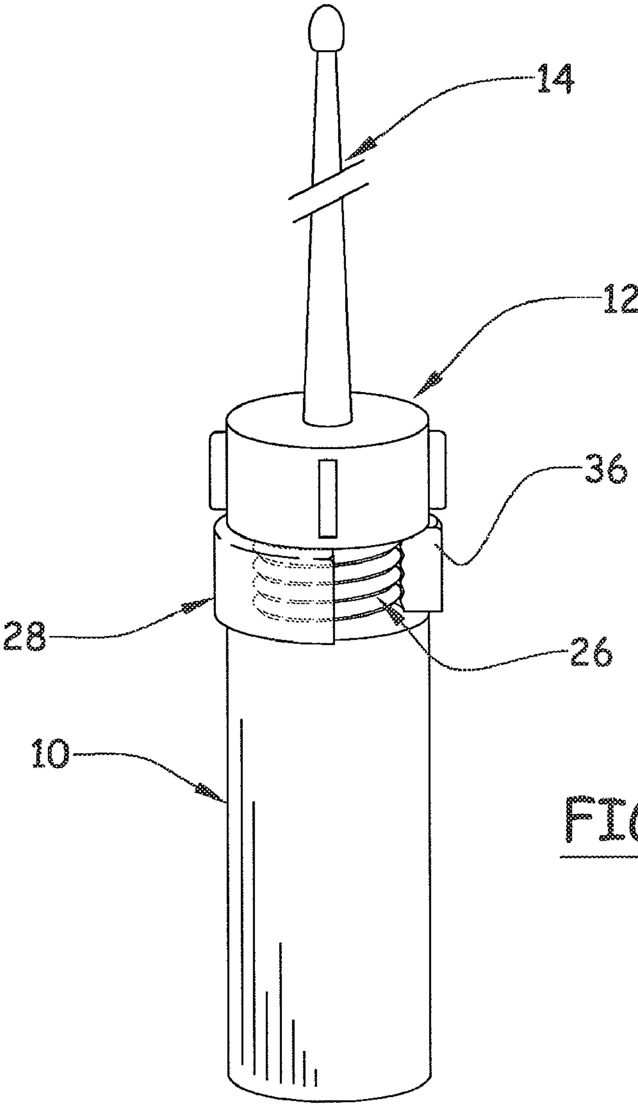

The present invention relates to a device for packaging and mucosal administration of active principles.

Methods exist of diffusing active principles by sublingual and/or paragingival permeation that offer numerous advantages.

Such diffusion methods enable action to be obtained much more quickly, with much smaller doses of active principles and in a much more targeted manner, thereby eliminating very many side effects. These side effects are generated in particular by the fact that medicines for oral administration are metabolized by various digestive organs prior to diffusing towards the intended targets of their active principles.

Although mucosal administration is a particularly attractive technique, it nevertheless remains associated with constraints that need to be mitigated in order to enable it to be easy for patients to use.

The active principles in solution, in particular in alcohol-based solutions, need to be packaged in single doses, said packaging also needing to be suitable for enabling mucosal, or sublingual, or paragingival administration.

A first constraint is the extremely small volume of the dose that is to be administered, of the order of 0.25 milliliters (mL) to 2 mL, to give an order of magnitude.

The solution is also fragile with respect to light and/or air, suffering from oxidation phenomena and being sensitive to evaporation phenomena. The solution may also be subject to absorption or ionization phenomena in contact with the walls of the container, thus making it necessary to use materials that are inert and particularly protective.

However, the solution, particularly when an alcohol-based solution, must conserve its degree of alcohol and constant dissolution stability for the packaged active principle(s), since these parameters are adapted for good permeation. Furthermore, the degree of alcohol is adjusted so as to conserve the active principles themselves.

It is important to conserve the initially designed degree of alcohol.

Furthermore, for certain unstable pharmacological substances, it is necessary for them to be dissolved only extemporaneously, i.e. at the time of administration, otherwise they are spoilt and thus no longer active.

An ever present constraint for such single-dose packaging is the cost of manufacture, which cost needs to be extremely small given the number of packages to be made and because each package is used on a single occasion only. It is also necessary to encourage recycling after use. Nevertheless, the packaging must comply with requirements concerning safety and asepsis, in particular while providing the looked-for practical and ergonomic features needed to guarantee that self-medication can be made easily available.

That is why the present invention provides a container for preparing and/or administering a very small volume of active principles in liquid form, the container comprising a head suitable for taking up a conservation, first position in which said head is in a distal position relative to the container, and an administration, second position in which said head is in a proximal position relative to the container, said head including a cannula with at least one flow channel, its length being adapted so that the free end of the flow channel can enable delivery by sublingual and/or paragingival permeation, while the container is being held in the hand.

The term "very small volume" is used to mean a volume for administration that lies in the range 0.1 mL to 5 mL.

The device is particularly suitable for preparing and administering active principles and/or antigen substances for pharmaceutical, homeopathic, and/or allergy desensitization treatments.

Figure 3:
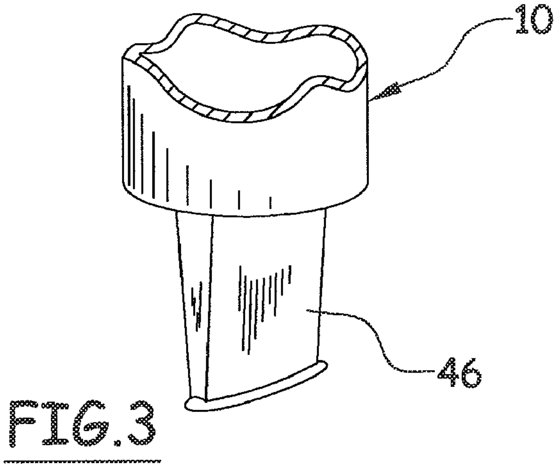
Figure 2A:
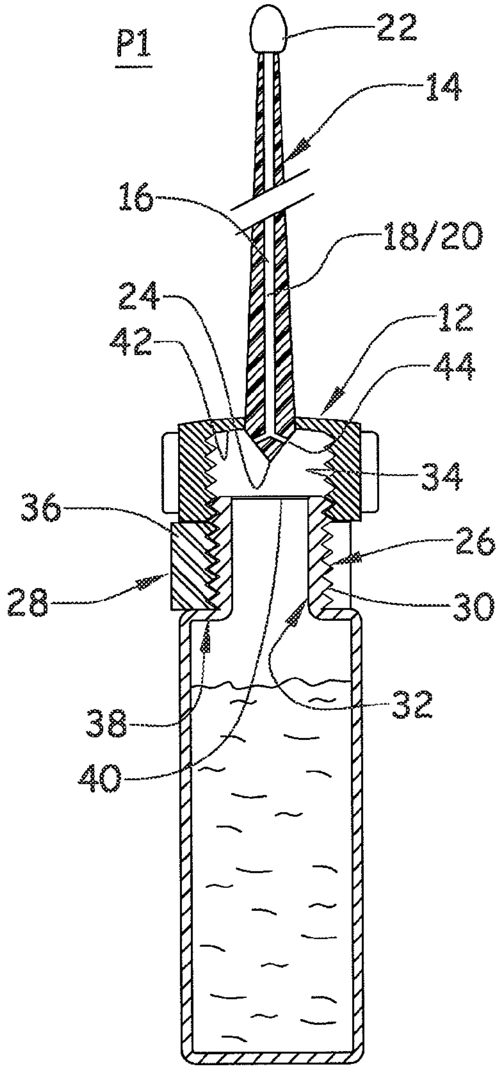
Figure 2B:
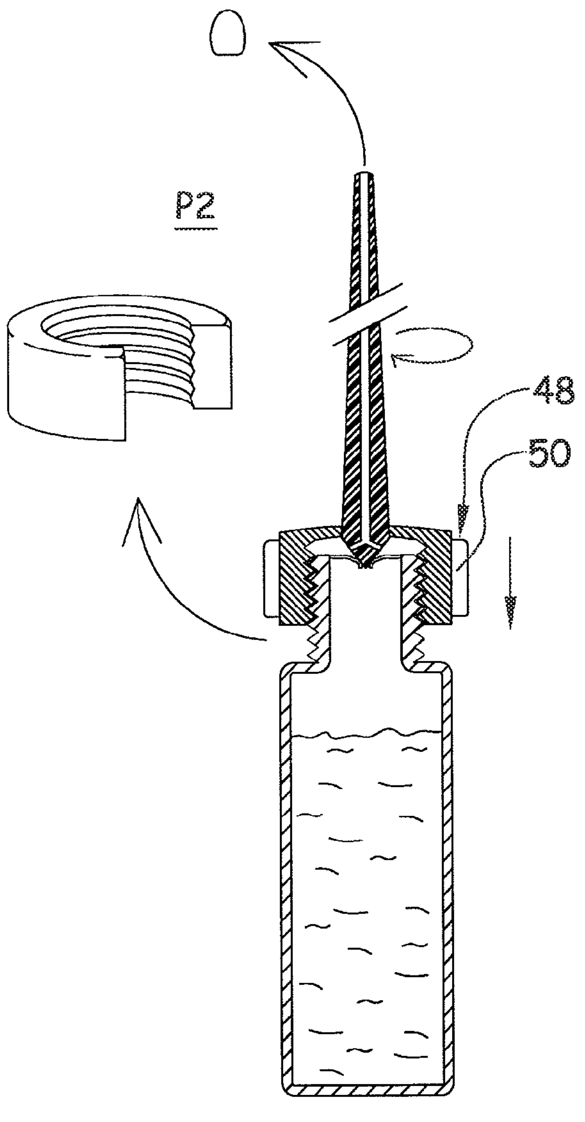
Figure 4:
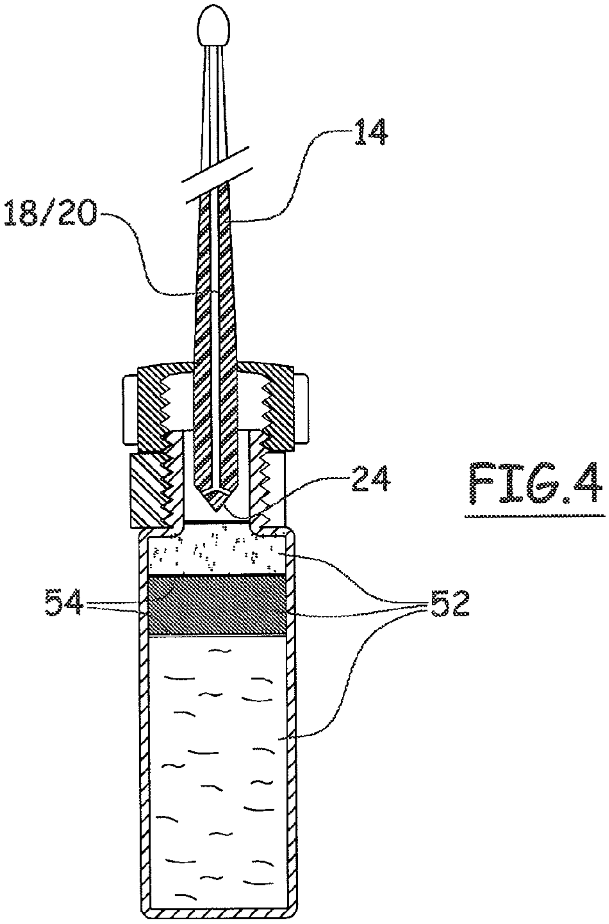
Figure 5A:
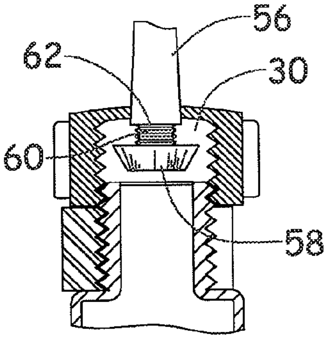
Figure 5B:
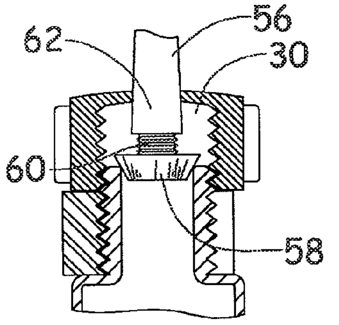
Figure 5C:
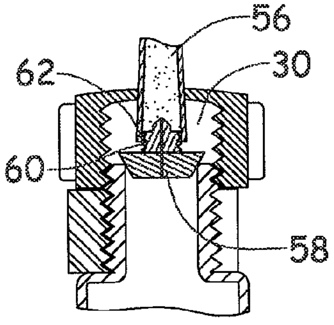

The packaging of the present invention is described below in detail in a particular, non-limiting embodiment, and with reference to the accompanying drawings, in which drawings, the various figures show:

FIG. 1: a perspective view from the side of the packaging of the present invention;

FIG. 2A: a section view of the packaging of the present invention, prior to any use, and ready for use;

FIG. 2B: a section view of the packaging of the invention after implementing various means enabling it to be used, ready for immediate therapeutic administration;

FIG. 3: packaging with a gripper and handling blade located at the bottom;

FIG. 4: a section view of variant packaging of the invention, having a plurality of compartments; and FIGS. 5A to 5C: a diagrammatic summary of the operation of a variant of the packaging of the present invention.

FIG. 1 shows a container 10 that may be made of any material that prevents evaporation through its wall and that is suitable for preventing light from acting on its content.

Such a container may be made of any material adapted to the intended applications and packaged substances, such as glass, metal, plastics material, or an association of these materials.

The container is advantageously made of glass, preferably thick, opaque glass of pharmaceutical quality, presenting high strength and a section that is square, oval, rectangular, triangular, or round.

In order to make the drawings clear, the items are voluntarily not drawn to scale.

The container 10 includes a head 12 that is secured thereto in movable manner, being free to move at least in translation relative to said container.

The head is suitable for taking a first position P1 for conservation in which said head 12 is in a distal position relative to the container 10, and a second position P2 for administration in which said head 12 is in a proximal position relative to the container 10.

The head 12 includes a cannula 14, having at least one flow channel 16.

Its length is such that the free end of the flow channel 16 can be received in particular under the tongue of the user or against the gum, while the container is being held in the hand.

In addition to the flow channel 16, the cannula 14 has at least one air intake 18, e.g. a second channel 20. The second channel 20 may be coaxial and outside the first channel 16, or it may be juxtaposed therewith, for example. Air may also be taken in via the first channel, depending on its diameter, the liquid solution being an alcohol-based solution and thus having very low viscosity.

At its free end, the cannula 14 has a mouthpiece cover 22. The mouthpiece cover 22 is a sealed safety stopper, e.g. sealed and breakable by being twisted off in the first embodiment, or else by being pulled off or by being cut off.

The cannula 14 is secured to the head 12 and is advantageously made integrally with said head. The material may be suitable polymer material.

The cannula 14 includes perforation means 24 at its root.

The container 10 and the head 12 are fitted with means 26 for enabling said head 12 to move in translation from the distal position to the proximal position.

The container is also provided with safety locking means 28 so as to prevent any unwanted movement in translation of the head 12 relative to the container 10.

In the preferred embodiment, the means 26 for movement in translation comprise an assembly of a screw thread 30 carried by the container 10, more particularly by the neck 32 of the container, and a tapping 34 of profile complementary to the screw thread of the container and carried by the head 12 so as to co-operate therewith by screw fastening.

The locking means 28 comprise a removable ring 36 interposed between the head 12 in the distal position and the container 10, more particularly the shoulder 38 of said container when it has one, and as shown in the embodiment of FIGS. 1 and 2.

The ring 36 has a C-shaped profile and is mounted elastically on the screw thread 30 carried by the container 10, thereby preventing the head 12 from moving in translation relative to the container 10.

In complementary manner, the opening of the neck 32 of the container 10 is provided with a sealed capsule 40 suitable for being perforated by the perforation means 24.

Advantageously, in order to ensure that all of the medicinal composition in liquid form is administered, the head 12 includes total flow means 42. These flow means 42 comprise internally a conical bottom, the cannula 14 being provided not only with the perforation means 24, but also with through holes 44 located immediately upstream from the bottom relative to the flow direction, and in communication with the flow channel 16. Under such circumstances, the perforation means 24 comprise solely a point.

Thus, the container 10 is filled with the medicinal composition in liquid form for mucosal administration and then the container 10 is closed in leaktight manner by putting the capsule 40 in position, which capsule then acts as a sealing membrane, particularly for an alcohol-based solution.

The ring 36 is placed on the neck around the screw thread 30, and then the head 12 is fitted on by screw fastening until it comes into abutment against the ring 36.

The mouthpiece cover 22 is in place on the cannula 14, closing the flow channel 16 and the channel 20 of the air intake 18.

In this conservation position, the packaging is not suitable for use and it may be stored without spoiling its content and without risk of being accessible to young children.

When the user seeks to self-administer the medicinal composition or to administer it to a third party, it suffices to remove the ring 36 merely by pulling it off and then to screw down the head 12.

This causes said head to move in translation, thereby causing the perforation means to tear the capsule that was providing sealing, thereby enabling the liquid to flow towards the cannula when the container is turned upside-down.

Removing the mouthpiece 22 before turning the container upside-down, e.g. by twisting said mouthpiece off, enables the composition to be delivered via the end of the cannula 14 positioned under the tongue or between the gum and the tongue or between the cheek and the gum, with the length of the cannula 14 being suitable for this purpose.

Thus, the composition is dispensed at exactly the location where it is most effective, with this applying to the entire volume contained.

It should be observed that the air intake enables the volume to be dispensed quickly, which volume, even though it is small, needs to be dispensed in a very short length of time, of the order of one second, to give an order of magnitude.

For this purpose, the inside diameter of the flow channel 16 needs to be relatively large, of the order of 2 millimeters for the above-mentioned quantities, lying in the range 0.25 mL to 2 mL. This proportionally large diameter can enable air to flow back therealong in order to facilitate fast flow.

When using a container of the thick glass bottle type, it is possible to make use of a special arrangement.

Either the neck carries a screw thread 30 formed together with the container, or else the neck is smooth. With a smooth neck, the movement means include a ferrule that is fastened directly in fixed manner on said neck of the container, e.g. by crimping, said ferrule having the screw thread 30 needed for co-operating with the tapping 34 in the head 12.

Under such circumstances, the glass container is filled with the composition and then the capsule is applied. Thereafter, the ferrule is fitted on the neck and is crimped, and then the ring 36 is positioned, and then the head 12 is in turn put into place.

For utilization, the user acts in exactly the same manner as described above.

As described above, the dimensions of the bottle are shown exaggerated in order to reveal details of its structure, but it should be understood that a container having a content of 0.25 mL to 2 mL is extremely small and difficult to handle.

Thus, the present invention proposes an improvement to the container, which improvement consists in adding a gripper blade 46 that is advantageously located at the bottom portion of the body of the container 10.

The gripper blade 46 enables a firm grip to be obtained between two fingers, in spite of the small size of the container, thus enabling the user to turn the head 12.

Similarly, the head 12 may include gripper means 48 on its peripheral outside surface, such as fins 50, as shown in the drawings.

The user can thus act by applying torque between the container 10 and the head 12.

It should also be observed that the gripper blade 46 also presents an advantage in handling after the head has been turned relative to the container and after the mouthpiece cover has been removed, by making it easy to handle the container when preparing it for use by positioning the cannula 14 in the desired location.

In a variant, the ring 36 may be a plastics collar suitable for being torn off or uncrimped. In order to make these operations of removing the collar easier, an external grippable pull tab may be added to the collar.

Similarly, prior to putting the capsule into place, filling may be performed under an inert gas atmosphere in order to preserve the content.

In another variant of the invention as shown in FIG. 4, the container 10 has at least two compartments 52, each compartment being separated by a leaktight capsule 54.

Each compartment contains at least an active principle, an excipient, an antigen substance, and/or a solvent.

The device also has perforation means 24 suitable for tearing the capsules 40 and/or 54, said means preferably being located at the root of the cannula 14 and/or in contiguity with the compartments 52 so as to be capable of causing the substances to be mixed together in a determined order.

When the user desires to administer the medicinal composition, the user pulls off the ring 36 and then screws down the head 12. This causes said head to move in translation, thereby causing the perforation means to tear the capsule(s) 40 and/or 54, thus enabling the substances contained in each of the compartments 52 to mix so as to obtain a liquid that flows towards the cannula when the container is turned upside-down.

The head 12 may also contain an active principle, an excipient, an antigen substance, and/or a solvent, e.g. in the cannula 14. The head 12 may also present a plurality of compartments separated by a capsule 66.

The substance contained in the head 12 may be in the form of a powder, a tablet, a lyophilized tablet, a liquid microcapsule, etc. When the head moves in translation, the perforation means tear the capsule(s) 40 and/or 54 and/or 66 enabling the substances contained in the head 12, in particular in the cannula 14, and in each of the compartments 52 to mix together. Similarly, if the substance contained in the head 12 is encapsulated, the perforation means tear the membrane encapsulating said substance prior to perforating the capsules 40 and/or 54 and/or 66.

The substance contained in the head 12 may also be in the form of a liquid contained in the cannula 14 of the head 12, as shown in FIG. 5. The cannula 14 then includes a top portion 56 containing the liquid sealed by a leakproof capsule 62, and a bottom portion 58, which portions are separated by a screw thread 60. Initial turning of the head 12 on the screw thread 30 causes the portion 28 to tear the capsule 40 that was sealing the container 10. Further turning causes the portion 58 to come into abutment against the screw thread 30. The cannula 14 then turns on the second screw thread 60, thereby tearing the capsule 62 that was sealing the cannula. The liquid in the head 12 is thus released and the substances that were previously separated can mix together.

These forms of container of the invention with at least two compartments 52 and/or a head 12 containing one or more substances, are particularly adapted to active principles and substances that are not stable in solution. This applies in particular to lipophilic active principles that, although perfectly soluble in water and alcohol solutions, present unstable behavior with the risk of becoming denatured and of forming undesirable compounds.

The container of the invention enables the active principle to be protected, i.e. the excipient and/or antigen substance in the form of a powder, a lyophilized tablet, a tablet, a liquid microcapsule, etc., and to achieve extemporaneous dissolution in a solvent immediately prior to administration. With certain complex components that spoil one another, it is thus possible to prepare a device having a plurality of separate compartments enabling these various poorly compatible substances to be assembled together in succession immediately before being administered, with this being done in a determined order.

The container of the invention may be used for preparing and/or administering active principles and/or antigen substances for purposes of pharmaceutical, homeopathic, and/or allergy desensitization treatments, in particular by passing via a mucous membrane.

The invention claimed is:

1. A device for preparing and/or administering by mucosal administration a very small volume of an alcohol based solution containing at least a lipophilic active principle, the device comprising a head and a container, the head being suitable for taking up a first conservation position P1 in which said head is in a distal position relative to the container, and a second administration, position P2 in which said head is in a proximal position relative to the container, said head including a cannula with at least one flow channel, the flow channel having a length permitting the free end of the flow channel to deliver the solution by sublingual and/or paragingival permeation while the device is being held in the hand; said device comprising at least two compartments, each compartment separated by a leakproof barrier, each compartment containing at least one or more of an active principle, an excipient, an antigen substance, and a solvent, said device further comprising perforation means for perforating the leakproof barrier; said perforation means formed on the cannula and in contiguity with the compartments so as to enable the substances contained in said compartments to be mixed together in a determined order; wherein the head includes one or more of an active principle, an antigen substance, an excipient, and a solvent; and wherein, prior to the perforation means perforating the leakproof barrier, the one or more of the active principle, the antigen substance, the excipient, and the solvent are contained in a space defined at least in part by a wall within the head that moves with the head during at least an initial part of a displacement of the head from the conservation position to the administration position.

2. The device according to claim 1, comprising movement means for moving the head in translation, these means comprising an assembly of a screw thread carried by said container and tapping of profile complementary to the screw thread of the container and carried by the head so as to co-operate by screw fastening.

3. The device according to claim 1, comprising safety locking means to prevent any unwanted movement in translation of the head relative to the container.

4. The device according to claim 3, wherein the locking means comprise a removable ring interposed between the head in the distal position and the container.

5. The device according to claim 1, wherein the cannula is provided with a mouthpiece cover for safety purposes that can be broken off.

6. The device according to claim 1, comprising a neck, and the opening of the neck is provided with a leakproof barrier.

7. The device according to claim 1, comprising a gripper blade located at the bottom portion of the body of the container so as to enable it to be gripped securely between two fingers.

8. The device according to claim 1, wherein the head includes gripper means on its peripheral outside surface.

9. The device according to claim 1, suitable for administering active principles and/or antigen substances for the purposes of pharmaceutical, homeopathic, and/or allergy desensitization treatments.

10. The device according to claim 9, adapted for mucosal administration.

11. The device according to claim 1, wherein the perforation means is formed at the root of the cannula.

12. A device for preparing and administering by mucosal administration a solution, the device comprising:

a reservoir comprising at least two compartments, each compartment separated by a leakproof barrier, wherein each compartment contains at least one or more substances;

a head displaceable relative to the reservoir between a first position and a second position;

a cannula that is a part of the head, the cannula comprising at least one flow channel configured to deliver the solution by sublingual or paragingival permeation while the device is held by hand;

a perforation tip that perforates the leakproof barrier for each compartment, the perforation tip formed on the cannula and displaceable with the cannula when the head is displaced between the first position and the second position so that the substances contained in the compartments are mixed together in a determined order to form the solution; wherein the head includes one or more of an active principle, an antigen substance, an excipient, and a solvent; and wherein, prior to the perforation tip perforating the leakproof barrier, the one or more of the active principle, the antigen substance, the excipient, and the solvent are contained in a space defined at least in part by a wall within the head that moves with the head during at least an initial part of the displacement between the first position and the second position.

13. The device according to claim 12, wherein the solution formed by mixture of the substances contained in the compartments is an alcohol based solution containing at least a lipophilic active agent.

14. The device according to claim 12, wherein a volume the of the solution formed by mixture of the substances contained in the compartments is about 0.25-2 ml.

15. The device according to claim 12, wherein the perforation tip is a one-piece integral construction with the cannula.

16. The device according to claim 12, wherein the perforation tip is a conical point at one end of the cannula.

17. The device according to claim 12, wherein the perforation tip comprises flow passages fluidly connecting the reservoir to the flow channel when the barrier for each compartment is perforated by the perforation tip.

18. The device according to claim 12, wherein the head is displaceable relative to the reservoir via a threaded coupling.

19. The device according to claim 12, further comprising a removable penannular ring between a portion of the head and the reservoir that blocks displacement of the head relative to the reservoir.

20. The device according to claim 12, further comprising a blade at a bottom end of the device and configured to be gripped by two fingers to enable twisting of the reservoir relative to the head.

21. The device according to claim 12, wherein the at least one or more substances are: an active principle, an excipient, an antigen, and a solvent.

* * * * *